United States Patent
Zou et al.

(10) Patent No.: US 12,050,225 B2
(45) Date of Patent: Jul. 30, 2024

(54) ULTRA-FAST AND HIGHLY-SENSITIVE CHEMILUMINESCENT IMMUNOASSAY METHOD FOR DETECTING THYROID STIMULATING HORMONE

(71) Applicant: Shandong University, Jinan (CN)

(72) Inventors: Guizheng Zou, Jinan (CN); Xiaoxuan Ren, Jinan (CN)

(73) Assignee: Shandong University, Jinan (CN)

( * ) Notice: Subject to any disclaimer, the term of this patent is extended or adjusted under 35 U.S.C. 154(b) by 0 days.

(21) Appl. No.: 18/317,488

(22) Filed: May 15, 2023

(65) Prior Publication Data
US 2024/0133902 A1 Apr. 25, 2024

(51) Int. Cl.
*G01N 33/76* (2006.01)
*G01N 33/543* (2006.01)

(52) U.S. Cl.
CPC ....... *G01N 33/76* (2013.01); *G01N 33/54326* (2013.01); *G01N 2333/59* (2013.01)

(58) Field of Classification Search
CPC ............. G01N 33/76; G01N 33/54326; G01N 2333/59
See application file for complete search history.

(56) References Cited

FOREIGN PATENT DOCUMENTS

| CA | 1116079 A | 1/1982 |
|---|---|---|
| CN | 1869152 A | 11/2006 |
| CN | 102662049 A | 9/2012 |
| CN | 112710645 A | 4/2021 |
| CN | 113702638 A | 11/2021 |
| CN | 114275806 A | 4/2022 |
| CN | 114384246 A | 4/2022 |

OTHER PUBLICATIONS

Dong et al. ("Glow and Flash Adjustable Chemiluminescence with Tunable Waveband from the Same CulnS2@ZnS Nanocrystal Luminophore", Anal. Chem., 2022, vol. 94, pp. 6902-6908) (Year: 2022).*
Ren et al. ("Enhanced Photon Emission of Chemiluminescent Luminophore for Ultra-Fast and Semi-Automatic Immunoassay toward Single Molecule Detection", Anal. Chem. 2023, vol. 95, pp. 8070-8076) (Year: 2023).*
Wang Jingxi, et al Electrochemiluminescence immunosensor for β-amyloid protein based on Luminol-modified AuAg@MnO_2 nanocomposites Chemical Sensors Issue 04, Dec. 15, 2016.
Lu Longfei, et al The review of chemiluminescense immunassay Journal of Molecular Diagnosis and Therapy Issue 05 Sep. 18, 2015.

* cited by examiner

*Primary Examiner* — Shafiqul Haq
*Assistant Examiner* — Nam P Nguyen
(74) *Attorney, Agent, or Firm* — CBM PATENT CONSULTING, LLC (57) ABSTRACT

An ultra-rapid and highly-sensitive chemiluminescence immunoassay for the detection of thyroid stimulating hormone uses water-soluble CdTe QDs as a chemiluminescence reagent and PBS solution of $KMnO_4$ with specific concentration and pH as an activator to construct a CdTe QDs/$KMnO_4$ chemiluminescence system of nanoparticle luminescence; based on the semi-automatic test method, the ultra-fast and highly sensitive detection of TSH can reach the level of single molecule detection.

7 Claims, 5 Drawing Sheets

ULTRA-FAST AND HIGHLY-SENSITIVE CHEMILUMINESCENT IMMUNOASSAY METHOD FOR DETECTING THYROID STIMULATING HORMONE

CROSS-REFERENCE TO RELATED APPLICATIONS

This application claims priority to Chinese Patent Application Ser. No. CN2022112763677 filed on 19 Oct. 2022.

TECHNICAL FIELD

The present invention relates to an ultra-fast and highly-sensitive chemiluminescent immunoassay method for detecting thyroid stimulating hormone, and belongs to the technical field of chemiluminescent immunoassay.

BACKGROUND

In the case of the continuous attack of coronavirus disease (COVID-19), the ultra-fast and highly-sensitive detection of the virus has become a general trend. Currently, practical COVID-19 detection methods are mainly realized by the nucleic acid amplification technology, which is time-consuming and requires using complicated devices. As an in vitro diagnostic technology with the advantages of high sensitivity, high specificity, wide linear range and simple instrumentation, chemiluminescent immunoassay (CLIA) has replaced the traditional enzyme-linked immunoassay in the field of in vitro diagnosis, and it is widely applied in the field of commercial immunoassay. All the labels used in the commercial CLIA are molecular luminescent substances, and only molecular reactive chemiluminescence can be implemented in the process of analysis and determination, such as luminol, acridinium ester and adamantane. Due to the fact that molecular luminescent reagents can participate in chemiluminescent reaction only once and the radiation signal is also weak, the current commercial CLIA cannot achieve the highly-sensitive and ultra-fast determination of targets.

Quantum dots (QDs) are a kind of nanomaterials with a size of 1-20 nm and consisting of IV, II-VI, IV-VI or III-V elements. QDs, which can be repeatedly excited by excited light to produce strong photoluminescence, have been the star material of photoluminescent probes since 1998 (Science, 1998, 281, 2016), and have been widely applied in the fields of fluorescent biochemical analysis and single molecule detection (Coord. Chem. Rev. 2014, 263, 86.). Studies on QDs as a chemiluminescent reagent and luminophor begun in 2004 (Nano Lett. 2004, 4, 693), and QDs have been used as labels for chemiluminescent immunoassay in recent years. However, limited by detection conditions and experimental techniques, the detection time of CLIA using QDs as a luminescent reagent is usually longer than 1 hour, which is inconsistent with the "fast" characteristic in individualized medicine, and the detection sensitivity has not reached the level of high sensitivity or even single molecule detection.

It is essential to develop an ultra-fast and highly-sensitive chemiluminescent immunoassay method without reducing the detection stability.

SUMMARY

In order to overcome the disadvantages of the prior art, especially the limitation that CLIA is hard to realize the highly-sensitive and ultra-fast detection of targets, the present invention provides an ultra-fast and highly-sensitive chemiluminescent immunoassay method for detecting thyroid stimulating hormone.

In the present invention, water-soluble CdTe QDs are used as a chemiluminescent reagent and the PBS solution of $KMnO_4$ with a specific concentration and a specific pH value is used as an excitant to construct a CdTe QDs/$KMnO_4$ chemiluminescence system of nanoparticle luminescence to implement the ultra-fast and highly-sensitive detection of targets, achieving a single molecule detection level which is hard to realize for traditional CLIA. The detection method has a very short detection time which is less than or equal to 6 min, can realize the detection of TSH at an ultra-fast speed, and has high sensitivity, wide detection range and low detection limit at the same time.

Notes of Terms:

TSH: Thyroid stimulating hormone.

Primary antibody (TSH-$Ab_1$): The primary antibody ($Ab_1$) in the present invention refers to an antibody corresponding to a biotin-labeled TSH antigen, and the present invention has a better effect on the monoclonal antibody corresponding to the antigen.

Secondary antibody (TSH-$Ab_2$): The second antibody in the present invention refers to a secondary antibody corresponding to the TSH antigen and the primary antibody.

EDC: 1-(3-Dimethylaminopropyl)-ethylcarbodiimide hydrochloride.

NHS: 1-Hydroxypyrrolidine-2,5-dione.

MCE: β-Mercaptoethanol.

PBS: It is short for phosphate buffered saline, and the main ingredients include $K_2HPO_4$, $KH_2PO_4$ and KCl.

PBST: It is short for PBS-Tween solution, and the main ingredients include $K_2HPO_4$, $KH_2PO_4$, KCl and Tween-20.

The present invention is realized by the following technical solution:

An ultra-fast and highly-sensitive chemiluminescent immunoassay method for detecting thyroid stimulating hormone, with a detection time of less than or equal to 6 min, including the following steps:

(1) preparing an immune complex
 1) re-dissolving purified water-soluble CdTe NCs in a PBST solution to obtain a CdTe NCs dispersing solution, adding a solution containing EDC and NHS to the dispersing solution to activate carboxyl groups for 10-15 min, adding diluted MCE, allowing reaction for 4-8 min at room temperature, adding a TSH-$Ab_2$ solution after the reaction, mixing evenly and incubating for 1-4 h, performing glycine blocking, removing unlinked QDs and TSH-$Ab_2$ to obtain CdTe QDs-labeled TSH-$Ab_2$, redispersing the TSH-$Ab_2$ in the PBST solution to obtain a CdTe QDs-labeled TSH-$Ab_2$ solution;
 2) adding a biotinylated TSH-$Ab_1$ solution into a streptavidin-labeled magnetic bead solution, performing oscillatory reaction, and re-dissolving the reaction product in the PBST solution after cleaning to obtain a TSH-$Ab_1$-linked magnetic bead solution; and
 3) mixing the CdTe QDs-labeled TSH-$Ab_2$ solution and the TSH-$Ab_1$-linked magnetic bead solution with the TSH antigen solution of a standard known concentration to obtain an immune complex solution;

(2) placing the immune complex solution in a magnetic field for magnetic separation, using a PBS solution of $KMnO_4$ (a concentration of the $KMnO_4$ is 1-3 mmol/L) as an excitant, collecting chemiluminescence signals by an NRM-CL-200 semi-automatic chemiluminescence instrument, and drawing a standard curve of the chemiluminescence signals and the antigen concentrations; and (3) replacing the TSH antigen solution of the standard known concentration by a target TSH antigen to be tested, constructing an immune complex according to the method in step (1), and then testing according to the method in step (2) to obtain a target electrochemiluminescence curve; and obtaining the TSH antigen in the sample solution to be tested according to the maximum light intensity and step standard curve of the obtained chemiluminescence curve.

According to the present invention, preferably in step 1), the PBST solution is 1 mL of PBST solution with a pH value of 7.4 and a concentration of 10 mmol/L, and a concentration of the CdTe NCs dispersing solution is 0.5-3 µmol/L.

According to the present invention, preferably in step 1), the solution containing EDC and NHS is a mixture of 20 µL of 100 mg/mL EDC solution and 20 µL of 100 mg/mL NHS solution.

According to the present invention, preferably in step 1), a concentration of the diluted MCE is 1-2 mol/L, and an addition amount of diluted MCE is 1-5 µL.

According to the present invention, preferably in step 1), a concentration of the TSH-$Ab_2$ solution is 5-15 µg/mL, and most preferably, the concentration of the TSH-$Ab_2$ solution is 10 µg/mL; and the solvent is a 10 mmol/L PBS buffer solution with a pH value of 7.4.

According to the present invention, preferably in step 1), an addition amount of the TSH-$Ab_2$ solution is 40-70 µL, and most preferably, the addition amount of the TSH-$Ab_2$ solution is 50 µL; and the inoculation is reaction at 37° C. for 2 h and coupling of the amino groups on the TSH-$Ab_2$ with the activated carboxyl groups on the quantum dots.

According to the present invention, preferably in step 1), the glycine blocking is to add 10 µL of 1% glycine to block the carboxyl activation sites for 2-3 h, centrifugate the solution, and wash the solution 3 times by the 10 mmol/L PBST solution with a pH value of 7.4 to remove unlinked QDs and TSH-$Ab_2$.

According to the present invention, preferably in step 1), the PBS buffer solution is prepared by the following method:
weighing 0.1867 g of $K_2HPO_4$, 0.0259 g of $KH_2PO_4$ and 0.0749 g KCl, and dissolving in 100 mL of deionized water to prepare the 10 mmol/L PBS buffer solution with a pH value of 7.4.

According to the present invention, preferably in step 1), the PBST solution is prepared by the following method:
adding 50 µL of Tween-20 to 100 mL of 10 mmol/L PBS buffer solution with a pH value of 7.4, and then mixing evenly to prepare the PBST solution.

According to the present invention, preferably in step 1), a concentration of the CdTe QDs-labeled TSH-$Ab_2$ solution is 0.5-3 µmol/L.

According to the present invention, preferably in step 2), the water-soluble CdTe NCs is the prior art in this field.

According to the present invention, preferably in step 2), a concentration of the streptavidin-labeled magnetic bead solution is 0.6-0.8 mg/mL, and the solvent is the 10 mmol/L PBS buffer solution with a pH value of 7.4; a concentration of the biotinylated TSH-$Ab_1$ solution is 1-4 µg/mL, and the solvent is the 10 mmol/L PBS buffer solution with a pH value of 7.4; and a volume ratio of the streptavidin-labeled magnetic bead solution to the biotinylated TSH-$Ab_1$ solution is (1-2): (1-2).

According to the present invention, preferably in step 2), the oscillatory reaction is oscillatory reaction at 37° C. for 30 min on a magnetic rack, the cleaning is cleaning by the 10 mmol/L PBST solution with a pH value of 7.4 5 times, and the TSH-$Ab_1$-linked magnetic bead solution with a concentration of 1-2 mg/mL is obtained by re-dissolving in 100 µL of PBS solution.

According to the present invention, preferably in step 3), the solvent of the TSH antigen solution with the standard known concentration is the 10 mmol/L PBS buffer solution with a pH value of 7.4; a volume ratio of the CdTe QDs-labeled TSH-$Ab_2$ solution to the TSH-$Ab_1$-linked magnetic bead solution to the TSH antigen solution with the standard known concentration is (2-4): (0.5-2): (1-3).

According to the present invention, preferably in step 3), specifically, 5-15 µL of TSH-$Ab_1$-linked magnetic bead solution and 15-25 µL of TSH antigen aqueous solution are evenly mixed with 130-150 µL of PBST buffer solution, 20-40 µL of CdTe QDs-labeled TSH-$Ab_2$ solution is added and evenly mixed, and oscillatory reaction is performed at room temperature for 4-5 min to obtain the immune complex solution.

The immune complex can be successfully obtained within 5 minutes of reaction at room temperature, and the reaction time is short.

According to the present invention, preferably, the biotinylated TSH-$Ab_1$, the TSH-$Ab_2$ and the TSH antigen are conventional and commercially available products, which can be purchased from Shanghai Medix Medical Technology Co., Ltd.; and the streptavidin-labeled magnetic beads are conventional and commercially available products, which can be purchased from Thermo Fisher Technology (China) Co., Ltd.

According to the present invention, preferably in step (2), a $KMnO_4$ concentration in the PBS solution of $KMnO_4$ is 1-2 mmol/L, an addition amount of the PBS solution of $KMnO_4$ is 20-40 µL, and a pH value is 7-7.4.

Most preferably, the $KMnO_4$ concentration in the PBS solution of $KMnO_4$ is 1.5 mmol/L, and the pH value is 7.4.

In the experiment, the inventor accidentally found that in the present invention, the $KMnO_4$ concentration was the key to the ultra-fast and highly-sensitive detection of TSH, an over-high or over-low concentration would lead to prolonged luminescence time, thereby resulting in a detection time longer than 6 min or even longer than 1 hour. The $KMnO_4$ concentration in the present invention makes the detection time quite short, so that the detection of TSH can be achieved very quickly.

According to the present invention, preferably in step (2), the PBS solution of $KMnO_4$ is prepared by the following method:
dissolving 0.0024 g of $KMnO_4$ in 10 mL of 10 mmol/L PBS buffer solution to obtain the 1.5 mmol/L PBS solution of $KMnO_4$.

In the present invention, the NRM-CL-200 semi-automatic chemiluminescence instrument for detection is provided by Nanjing Norman Biotechnology Co., Ltd.

The present invention has the following technical features and advantages:
1. A reaction time of CLIA is usually 1-3 hours; in the present invention, water-soluble CdTe QDs are used as a chemiluminescent reagent and the PBS solution of $KMnO_4$ with a specific concentration and a specific pH value is used as an excitant to construct a CdTe QDs/$KMnO_4$ chemiluminescence system of nanoparticle luminescence to implement the ultra-fast and highly-sensitive detection of targets, achieving a single molecule detection level which is hard to realize for traditional CLIA. The detection method has a very short detection time, a reaction time of the immune complex of the present invention is within 5 min, and a collection time of chemiluminescence signals is within 50 s, with a total time not exceeding 6 min.

2. The sensitivity of traditional CLIA is hard to reach the level of single molecule detection. The chemiluminescent immunoassay of the present invention shows a good linear relationship within a concentration range of 0.0075 fg/ml-1 fg/mL, and a detection limit is 0.0075 fg/mL. It breaks through the current situation that automatic and semi-automatic chemiluminescent immunoassay cannot implement single molecule detection.

3. Currently, molecular luminescent reagents are used in commercial CLIA. The reagents react to become other substances and cannot sustain chemiluminescence with a weak radiation signal; in the present invention, the nanomaterial CdTe QDs is used as a luminescent reagent and the PBS solution of $KMnO_4$ with a specific concentration is used as an excitant to continuously generate chemiluminescent reaction, so as to implement the strategy of luminescence signal amplification, improve the detection sensitivity to the level of single molecule, and effectively shorten the detection time.

4. In the present invention, the chemiluminescence signal values are tested by the NRM-CL-200 semi-automatic chemiluminescence instrument produced by Nanjing Norman Biological Technology Co., Ltd. The CdTe QDs have strong chemiluminescence intensity and short luminescence time (within 0.5 s), belonging to flash-type chemiluminescence.

DETAILED DESCRIPTION OF THE EMBODIMENTS

The present invention will be further explained in combination with, but is not limited by, the embodiments.

In the embodiments, the biotinylated TSH-$Ab_1$, the TSH-$Ab_2$ and the TSH antigen are conventional and commercially available products, which can be purchased from Shanghai Medix Medical Technology Co., Ltd.; and the streptavidin-labeled magnetic beads are conventional and commercially available products, which can be purchased from Thermo Fisher Technology (China) Co., Ltd.

In the embodiments, the electrochemiluminescence intensity curve is collected and acquired by the NRM-CL-200 semi-automatic chemiluminescence instrument produced by Nanjing Norman Biotechnology Co., Ltd.

In the embodiments, the water-soluble CdTe NCs are prepared by the following method:
(1) taking 1.6 mL of 0.1 mol/L $CdCl_2 \cdot 2H_2O$ solution, diluting the $CdCl_2 \cdot 2H_2O$ solution to 50 mL by adding deionized water, and stirring at room temperature;
(2) adding 293.6 mg of sodium hexametaphosphate to the mixture prepared in step (1);
(3) adding 36.4 μL of mercaptopropionic acid to the mixture prepared in step (2);
(4) adding 1 M of sodium hydroxide to the mixture prepared in step (3) to adjust a pH value to 8.0;
(5) adding 5.3 mg of sodium tellurite to the mixture prepared in step (4), and refluxing at 100° C. for 10 min; and
(6) adding 2.4 mL of hydrazine hydrate to the mixture prepared in step (5), and refluxing at 100° C. for 24 h.

In the embodiments, the PBS buffer solution is prepared by the following method: weighing 0.1867 g of $K_2HPO_4$, 0.0259 g of $KH_2PO_4$ and 0.0749 g of KCl, and dissolving in 100 mL of deionized water to prepare the 10 mmol/L PBS buffer solution with a pH value of 7.4.

In the embodiments, the PBST buffer solution is prepared by the following method: adding 50 μL of Tween-20 to 100 mL of the prepared 10 mmol/L PBS buffer solution with a pH value of 7.4, and then mixing evenly to prepare the 10 mmol/L PBST solution with a pH value of 7.4.

EXAMPLE 1

An ultra-fast and highly-sensitive chemiluminescent immunoassay method for detecting thyroid stimulating hormone, with a detection time of less than or equal to 6 min, included the following steps:
(1) an immune complex was prepared
1) 1 mL of CdTe stock solution was purified and then re-dissolved in 1 mL of 10 mmol/L PBST solution with a pH value of 7.4, and 20 μL of 100 mg/mL EDC solution and 20 μL of 100 mg/mL NHS solution were mixed and added to activate carboxyl groups for 10-15 min; 1.5 μL of 1.45 mol/L MCE diluent was added and mixed evenly, and reaction was allowed at room temperature for 5 min; 50 μL of 10 μg/mL TSH-$Ab_2$ solution was added, the mixture was mixed evenly, reaction was allowed at 37° C. for 2 h, and the amino groups on the TSH-$Ab_2$ were coupled with the carboxyl groups on the quantum dots; then 10 μL of 1% glycine was added to block the carboxyl activation sites for 2-3 h, and the solution was centrifuged and washed with a PBST solution 3 times to remove excessive TSH-Ab$_2$, and then re-dispersed in 1 mL of PBST solution to obtain a CdTe QDs-labeled TSH-Ab$_2$ solution with a concentration of 1 µmol/L;

2) 200 µL of 0.75 mg/mL streptavidin-labeled magnetic bead solution was taken, 250 µL of 2 µg/mL biotinylated TSH-Ab$_1$ solution was added, oscillatory reaction was performed at 37° C. for 30 min on a magnetic rack, and the reaction product was cleaned with 10 mmol/L PBST solution with a pH value of 7.4 5 times, and then re-dissolved in 100 µL of PBS solution to obtain a TSH-Ab$_1$-linked magnetic bead solution with a concentration of 1 mg/mL; and 3) 10 µL of TSH-Ab$_1$-linked magnetic bead solution was placed in a 96-well plate, 20 µL of TSH antigen solution was added, 140 µL of PBST buffer solution was added and mixed evenly, 30 µL of CdTe QDs-labeled TSH-Ab$_2$ solution was added, mixed evenly and oscillated at room temperature for 5 min to obtain an immune complex solution;

(2) the immune complex solution was placed in a magnetic field for magnetic separation, a PBS solution of KMnO$_4$ was added as an excitant, wherein a KMnO$_4$ concentration in the PBS solution of KMnO$_4$ was 1.5 mmol/L, and a pH value was 7.4; chemiluminescence signals were collected by an NRM-CL-200 semi-automatic chemiluminescence instrument, and a standard curve of chemiluminescence signals and antigen concentrations was drawn; and (3) the TSH antigen solution of the standard known concentration was replaced by a target TSH antigen to be tested, an immune complex was constructed according to the method in step (1) and then tested according to the method in step (2) to obtain a target electrochemiluminescence curve; and the TSH antigen in the sample solution to be tested was obtained according to the maximum light intensity and step standard curve of the obtained chemiluminescence curve.

EXAMPLE 2

An ultra-fast and highly-sensitive chemiluminescent immunoassay method for detecting thyroid stimulating hormone is the same as that in example 1, and the difference lies in that:
in step (2), a pH value of the PBS solution of KMnO$_4$ is 7.2.

EXAMPLE 3

An ultra-fast and highly-sensitive chemiluminescent immunoassay method for detecting thyroid stimulating hormone is the same as that in example 1, and the difference lies in that:
in step (2), a KMnO$_4$ concentration in the PBS solution of KMnO$_4$ is 1.8 mmol/L.

EXAMPLE 4

An ultra-fast and highly-sensitive chemiluminescent immunoassay method for detecting thyroid stimulating hormone is the same as that in example 1, and the difference lies in that:
in step (2), a KMnO$_4$ concentration in the PBS solution of KMnO$_4$ is 2.0 mmol/L.

EXPERIMENTAL EXAMPLE 1

Different contents of KMnO$_4$ were weighed and dissolved in 10 mL of 10 mmol/L PBS buffer solution with a pH value of 7.4, ultrasonic dissolution was performed for mixing the mixture evenly to obtain 0.5 mmol/L, 1.0 mmol/L, 1.5 mmol/L, 5 mmol/L and 10 mmol/L PBS solutions of KMnO$_4$, used as excitants;
purified water-soluble CdTe NCs were re-dissolved in 1 mL of 10 mmol/L PBST solution with a pH value of 7.4 to obtain a CdTe NCs dispersing solution with a concentration of 1 µmol/L; and
200 µL of each of the PBS solutions of KMnO$_4$ with different concentrations was evenly mixed with 100 µL of 1 CdTe NCs dispersing solution to obtain a CdTe QDs/KMnO$_4$ chemiluminescence system.

An NRM-CL-200 semi-automatic chemiluminescence instrument was used to collect chemiluminescence signals. The luminescence intensity of the CdTe QDs/KMnO$_4$ chemiluminescence systems containing the PBS solutions of KMnO$_4$ with different concentrations and the CdTe NCs dispersing solution is as shown in FIG. 1.

Figure 1:
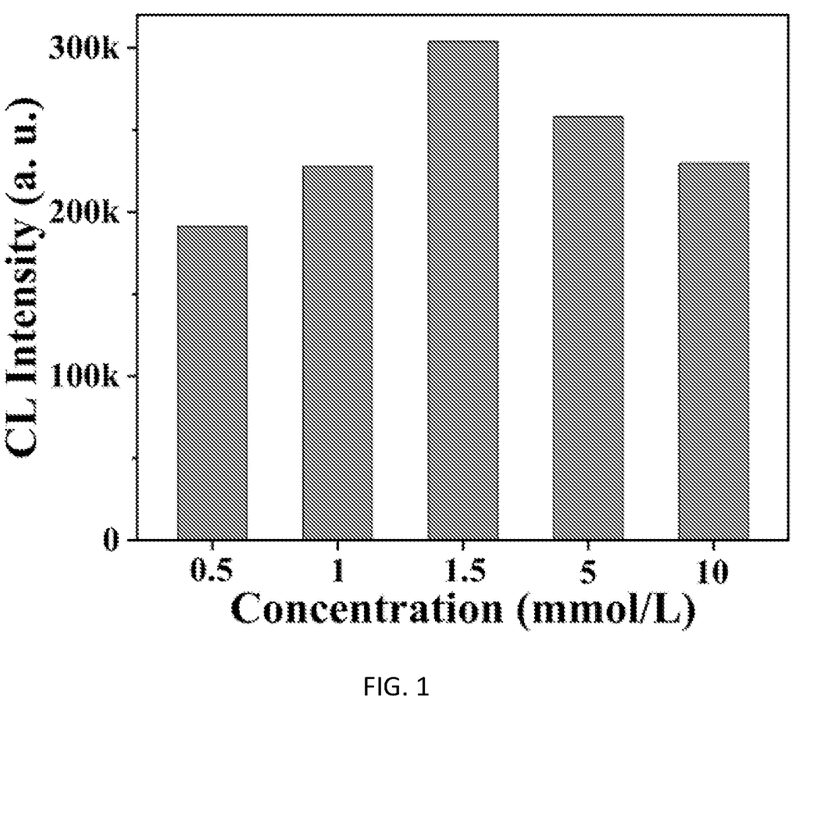
FIG. 1 is a diagram of effect of different concentrations of $KMnO_4$ on luminescence intensity in experimental example 1; the X-coordinate represents the $KMnO_4$ concentration, and the Y-coordinate represents the chemiluminescence intensity.

It could be known from FIG. 1 that all the 0.5 mM-15 mM excitants could generate chemiluminescence signals of a certain intensity, the chemiluminescence signals were gradually enhanced as the KMnO$_4$ concentration increased, and the 1.5 mM PBS solution of KMnO$_4$ as the excitant had the strongest chemiluminescence signals; however, the chemiluminescence signals were gradually reduced when the KMnO$_4$ concentration exceeded 2 mM. It can be seen that the chemiluminescence signals will be reduced if the KMnO$_4$ concentration is too high or too low.

EXPERIMENTAL EXAMPLE 2

KMnO$_4$ was weighed and dissolved in 10 mL of 10 mmol/L PBS buffer solution with different pH values, and ultrasonic dissolution was performed for mixing the mixture evenly to obtain PBS solutions of KMnO$_4$ with a KMnO$_4$ concentration of 1.5 mM and different pH values, used as excitants;
purified water-soluble CdTe NCs were re-dissolved in 1 mL of 10 mmol/L PBST solution with a pH value of 7.4 to obtain a CdTe NCs dispersing solution with a concentration of 1 µmol/L; and
200 µL of each of the PBS solutions of KMnO$_4$ with a KMnO$_4$ concentration of 1.5 mM and different pH values was evenly mixed with 100 µL of 1 µmol/L CdTe NCs dispersing solution to obtain a CdTe QDs/KMnO$_4$ chemiluminescence system.

An NRM-CL-200 semi-automatic chemiluminescence instrument was used to collect chemiluminescence signals. The luminescence intensity of the CdTe QDs/KMnO$_4$ chemiluminescence systems containing the PBS solutions of KMnO$_4$ with different pH values and the CdTe NCs dispersing solution is as shown in FIG. 2.

Figure 2:
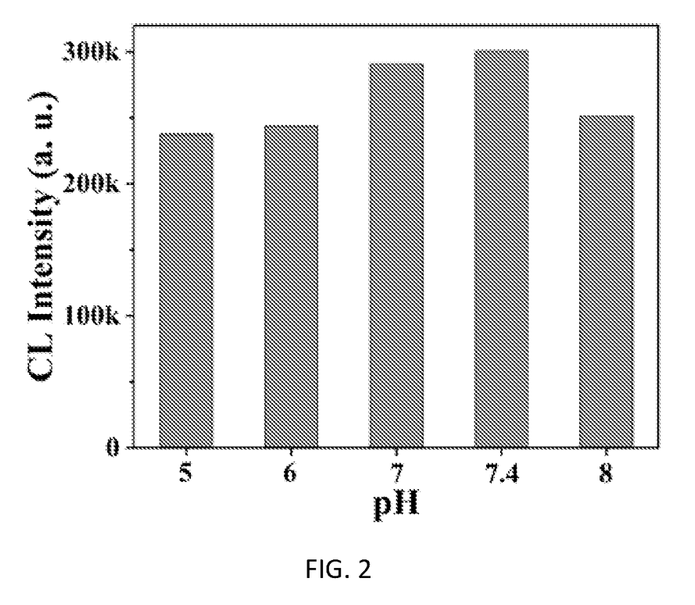
FIG. 2 is a diagram of effect of excitants with different pH values on luminescence intensity in experimental example 2; the X-coordinate represents the pH value, and the Y-coordinate represents the chemiluminescence intensity.

It could be known from FIG. 2 that the PBS solutions of KMnO$_4$ with a pH value of 7-7.4 had strong chemiluminescence signals, especially that the chemiluminescence signals were strong when the pH value was 7.4. It can be seen that the excitant with a pH value of 7.4 has the best effect, and the pH value of less than 7 or more than 7.4 will reduce the chemiluminescence signals.

EXPERIMENTAL EXAMPLE 3

200 μL of PBS solution of $KMnO_4$ with a $KMnO_4$ concentration of 1.5 mM and a pH value of 7.4 was evenly mixed with 100 μL of 1 μmol/L CdTe NCs dispersing solution to obtain a CdTe QDs/$KMnO_4$ chemiluminescence system, the CdTe QDs/$KMnO_4$ chemiluminescence system was placed in a chemiluminescence reaction cup, and a chemiluminescence intensity curve and a chemiluminescence spectrum curve were collected by an NRM-CL-200 semi-automatic chemiluminescence instrument.

Figure 3:
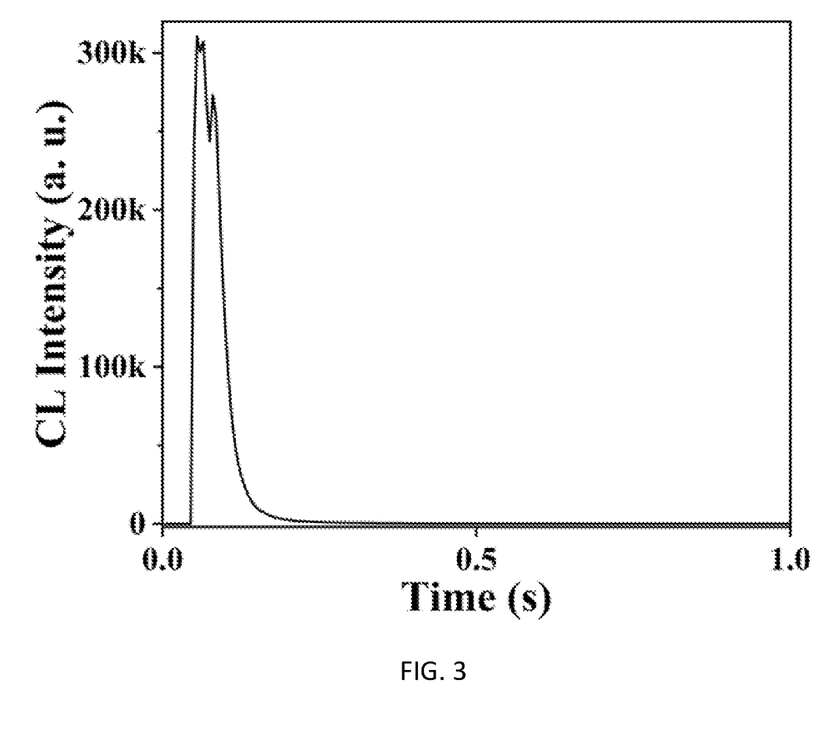
FIG. 3 is a chemiluminescence intensity curve of CdTe QDs prepared in experimental example 3; the X-coordinate represents the time, and the Y-coordinate represents the chemiluminescence intensity.
Figure 4:
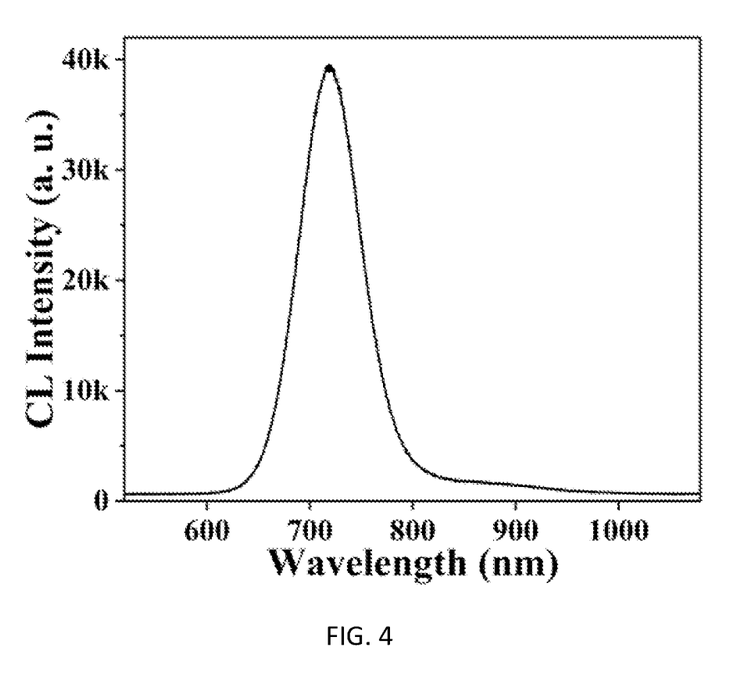
FIG. 4 is a chemiluminescence spectrum curve of CdTe QDs prepared in experimental example 3; the X-coordinate represents the wavelength, and the Y-coordinate represents the chemiluminescence intensity.

The chemiluminescence intensity curve of the CdTe QDs/$KMnO_4$ chemiluminescence system is as shown in FIG. 3, and the chemiluminescence spectrum curve is as shown in FIG. 4.

It could be known from FIG. 3 that the excitant of the present invention could react with CdTe QDs to produce chemiluminescence instantly when the excitant was injected into the reaction vessel. The luminescence time was within 0.5 s, and the system belonged to a flash-type chemiluminescence system. It could be known from FIG. 4 that in the present invention, a chemiluminescent radiation band generated by the CdTe QDs was about 700 nm.

EXPERIMENTAL EXAMPLE 4

100 μL of 1 μmol/L CdTe QDs-labeled TSH-$Ab_2$ solution obtain in step 1) of example 1 was taken and placed in a chemiluminescence reaction cup, and a chemiluminescence intensity curve after the excitant was injected was collected by an NRM-CL-200 semi-automatic chemiluminescence immunoanalyzer.

Figure 5:
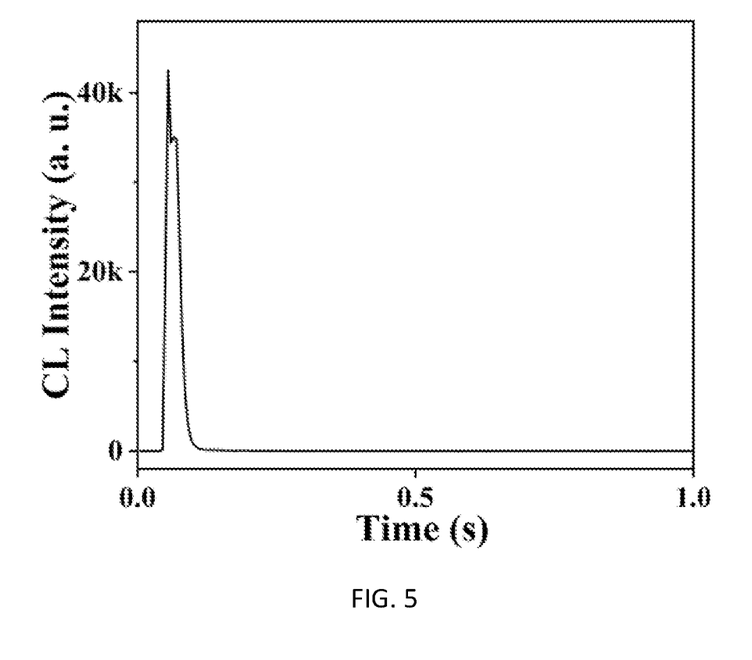
FIG. 5 is a chemiluminescence intensity curve of CdTe QDs-Ab 2 prepared in experimental example 4; the X-coordinate represents the time, and the Y-coordinate represents the chemiluminescence intensity.

A chemiluminescence spectrum curve of the CdTe QDs-labeled TSH-$Ab_2$ is as shown in FIG. 5.

It could be known from FIG. 5 that a chemiluminescent radiation band generated by the CdTe QDs-labeled TSH-$Ab_2$ showed a redshift as compared with that generated by the CdTe QDs, and the chemiluminescent radiation band was located at about 720 nm, indicating that the CdTe QDs-labeled TSH-$Ab_2$ was successfully labeled.

EXPERIMENTAL EXAMPLE 5

In step 3) of example 1, different concentrations of TSH antigen solutions were prepared as 0.0075 fg/mL, 0.01 fg/mL, 0.025 fg/mL, 0.1 fg/mL, 0.5 fg/mL and 1 fg/mL, respectively, to form immune complex solutions; the immune complex solutions were placed in a magnetic field for magnetic separation. 20 μL of each of the immune complex solutions of different concentrations was added into 30 μL of PBS solution of $KMnO_4$ with a $KMnO_4$ concentration of 1.5 mM and a pH value of 7.4, used as excitants; the excitants were transferred into chemiluminescence reaction cups, chemiluminescence spectrum curves and chemiluminescence signals were collected, and the obtained signal values of different TSH antigen concentrations were plotted into working curves.

Figure 6:
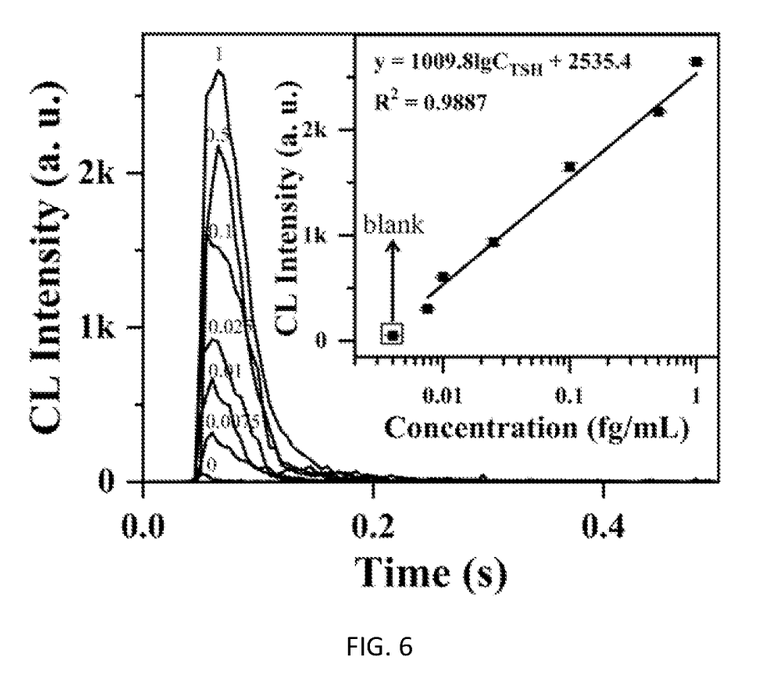
FIG. 6 is a working curve of TSH antigen detection in experimental example 5; the X-coordinate represents the TSH antigen concentration, and the Y-coordinate represents the chemiluminescence intensity.

The chemiluminescence spectrum curves and working curves of the TSH antigen solutions with different concentrations are as shown in FIG. 6. It could be known from FIG. 6 that the sensitivity of the chemiluminescent immunoassay method for detecting TSH of the present invention could reach 0.0075 fg/mL, and had a wide detection range.

EXPERIMENTAL EXAMPLE 6: Specific Detection

The detection method is the same as that in example 1, and the difference lies in that:

the TSH antigen was replaced by blank; carcinoembryonic antigen (CEA); prostate specific antigen (PSA); alpha-fetoprotein antigen (AFP); carbohydrate antigen (CA125); and a mixture of carcinoembryonic antigen (CEA), prostate specific antigen (PSA), alpha-fetoprotein antigen (AFP), carbohydrate antigen (CA125) and the TSH antigen.

Figure 7:
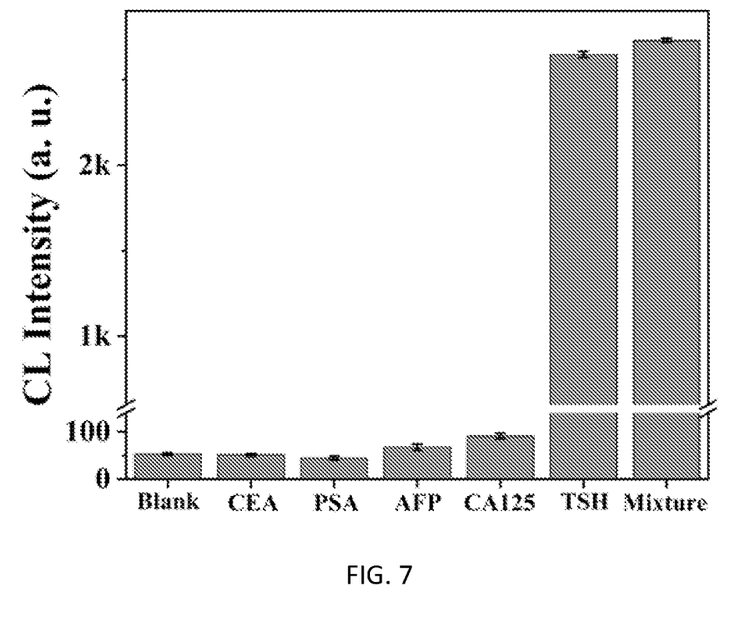
FIG. 7 is a diagram of chemiluminescence intensity when a TSH antigen concentration is 1 fg/mL in experimental example 6; the X-coordinate represents the time, and the Y-coordinate represents the chemiluminescence intensity.

The electrochemiluminescence responses of the different antigens are as shown in FIG. 7. As shown in FIG. 7, the detection method of the present invention had good selectivity for the TSH antigen, and other antigen proteins did not interfere with the TSH antigen, indicating that the detection method of the present invention is highly specific to detecting the TSH antigen.

EXPERIMENTAL EXAMPLE 7

Figure 8:
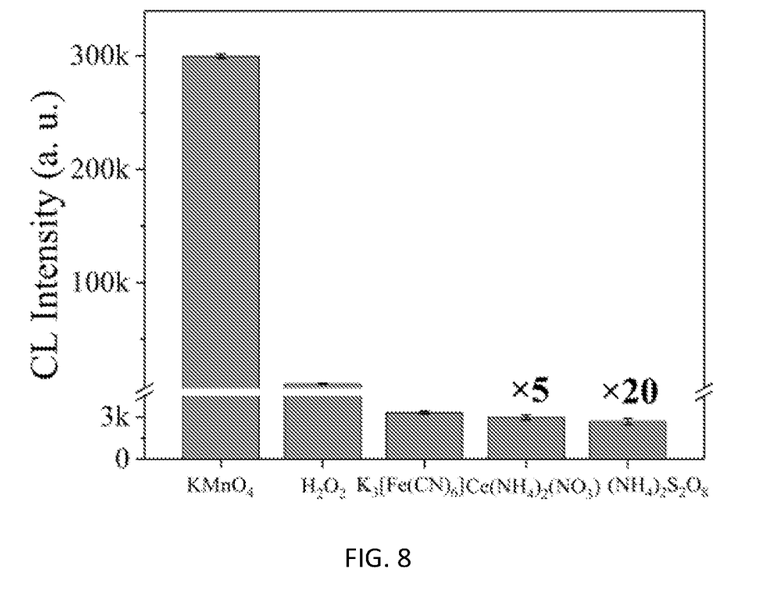
FIG. 8 is a diagram of luminescence intensity of a chemiluminescence system formed by different kinds of excitants in experimental example 7; the X-coordinate represents the time, and the Y-coordinate represents the chemiluminescence intensity.

Different kinds of excitants were prepared:
2.4 mg of $KMnO_4$ was weighed and dissolved in 10 mL of 10 mmol/L PBS buffer solution with a pH value of 7.4, and ultrasonic dissolution was performed for mixing the mixture evenly to obtain a 1 mmol/L PBS solution of $KMnO_4$, used as excitant 1;
3.263 mg of $K_3[Fe(CN)_6]$ was weighed and dissolved in 10 mL of 10 mmol/L PBS buffer solution with a pH value of 7.4, and ultrasonic dissolution was performed for mixing the mixture evenly to obtain a 1 mmol/L PBS solution of $K_3[Fe(CN)_6]$, used as excitant 2;
2.282 mg of $(NH_4)_2S_2O_8$ was weighed and dissolved in 10 mL of 10 mmol/L PBS buffer solution with a pH value of 7.4, and ultrasonic dissolution was performed for mixing the mixture evenly to obtain a 1 mmol/L PBS solution of $(NH_4)_2S_2O_8$, used as excitant 3;
109.644 mg of $Ce(NH_4)_2(NO_3)$ was weighed and dissolved in 10 mL of 10 mmol/L PBS buffer solution with a pH value of 6.6, and ultrasonic dissolution was performed for mixing the mixture evenly to obtain a 20 mmol/L PBS solution of $Ce(NH_4)_2(NO_3)$, used as excitant 4;
a 3 mol/L $H_2O_2$ solution was used as excitant 5; and
200 μL of each of the above excitants (excitants 1-5) was evenly mixed with 100 μL of 1 μmol/L CdTe NCs dispersing solution respectively, the mixtures were placed in chemiluminescence reaction cups respectively, and chemiluminescence signals were collected by an NRM-CL-200 semi-automatic chemiluminescence instrument; a chemiluminescence system was formed by the different excitants and the CdTe NCs dispersing solution, respectively. The luminescence intensities of the different excitants under optimal conditions are as shown in FIG. 8. As shown in FIG. 8, the PBS solution of $KMnO_4$ has the strongest chemiluminescence signals.

What is claimed is:
1. An ultra-fast and highly-sensitive chemiluminescent immunoassay method for detecting thyroid stimulating hormone, including the following steps:
(a) preparing an immune complex
i) re-dissolving purified water-soluble CdTe nanocrystals (NCs) in a phosphate buffered saline-Tween (PBST) solution to obtain a CdTe NCs dispersing solution, adding a solution containing 1-(3-dimethylaminopropyl)-ethylcarbodiimide hydrochloride (EDC) and 1-hydroxypyrrolidine-2,5-dione (NHS) to the dispersing solution to activate carboxyl groups for 10-15 min, adding diluted β-mercaptoethanol (MCE,) allowing reaction for 4-8 min at room temperature, adding a thyroid stimulating hormone sec- ondary antibody (TSH-Ab$_2$) solution after the reaction, mixing evenly and incubating for 1-4 h, performing glycine blocking, removing unlinked NCs and TSH-Ab$_2$ to obtain CdTe NCs-labeled TSH-Ab$_2$, redispersing the TSH-Ab2 in the PBST solution to obtain a CdTe NCs-labeled TSH-Ab$_2$ solution; wherein the water-soluble CdTe NCs contains 3-Mercaptopropionic acid (MPA) functionalized CdTe luminophores;

ii) adding a biotinylated thyroid stimulating hormone primary antibody (TSH-Ab$_1$) solution into a streptavidin-labeled magnetic bead solution, performing oscillatory reaction, and re-dissolving the reaction product in the PBST solution after cleaning to obtain a TSH-Ab$_1$-linked magnetic bead solution; and iii) mixing the CdTe NCs-labeled TSH-Ab$_2$ solution and the TSH-Ab$_1$-linked magnetic bead solution with the thyroid stimulating hormone (TSH) antigen solution of a standard known concentration to obtain an immune complex solution;

(b) placing the immune complex solution in a magnetic field for magnetic separation, using a PBS solution of KMnO$_4$ as an excitant, a concentration of the KMnO$_4$ is 1.5 mmol/L, an addition amount of the PBS solution of KMnO$_4$ is 20-40 µL, and the pH value is 7.4, collecting chemiluminescence signals by an NRM-CL-200 semi-automatic chemiluminescence instrument, and drawing a standard curve of the chemiluminescence signals and the antigen concentrations;

the PBS solution of KMnO$_4$ is prepared by the following method:

dissolving 0.0024 g of KMnO$_4$ in 10 ml of 10 mmol/L PBS buffer solution to obtain the 1.5 mmol/L PBS solution of KMnO$_4$;

(c) replacing the TSH antigen solution of the standard known concentration with a sample solution, constructing an immune complex according to the method in step (a), and then testing according to the method in step (b) to obtain a target electrochemiluminescence curve; and obtaining the concentration of the TSH antigen in the sample solution according to the maximum light intensity and step standard curve of the obtained chemiluminescence curve;

the PBS buffer solution is prepared by the following method:

weighing 0.1867 g of K$_2$HPO$_4$, 0.0259 g of KH$_2$PO$_4$ and 0.0749 g KCl, and dissolving in 100 mL of deionized water to prepare the 10 mmol/L PBS buffer solution with a pH value of 7.4;

wherein in step 1), the PBST solution is prepared by the following method:

adding 50 µL of Tween-20 to 100 ml of 10 mmol/L PBS buffer solution with a pH value of 7.4, and then mixing evenly to prepare the PBST solution.

2. The chemiluminescent immunoassay method according to claim 1, wherein in step i), the PBST solution is 1 mL of PBST solution with a pH value of 7.4 and a concentration of 10 mmol/L, and a concentration of the CdTe NCs dispersing solution is 0.5-3 µmol/L;

the solution containing EDC and NHS is a mixture of 20 µL of 100 mg/mL EDC solution and 20 µL of 100 mg/mL NHS solution;

a concentration of the diluted MCE is 1-2 mol/L, and an addition amount of diluted MCE is 1-5 µL;

a concentration of the TSH-Ab2 solution is 5-15 µg/mL, and the solvent is a 10 mmol/L PBS buffer solution with a pH value of 7.4;

an addition amount of the TSH-Ab$_2$ solution is 40-70 µL, and the inoculation is reaction at 37° C. for 2 h and coupling of the amino groups on the TSH-Ab$_2$ with the activated carboxyl groups on the quantum dots;

the glycine blocking is to add 10 µL of 1% glycine to block the carboxyl activation sites for 2-3 h, centrifugate the solution, and wash the solution 3 times by the 10 mmol/L PBST solution with a pH value of 7.4 to remove unlinked NCs and TSH-Ab$_2$.

3. The chemiluminescent immunoassay method according to claim 1, wherein in step i), a concentration of the CdTe NCs-labeled TSH-Ab$_2$ solution is 0.5-3 µmol/L.

4. The chemiluminescent immunoassay method according to claim 1, wherein in step ii), a concentration of the streptavidin-labeled magnetic bead solution is 0.6-0.8 mg/mL, and the solvent is the 10 mmol/L PBS buffer solution with a pH value of 7.4; a concentration of the biotinylated TSH-Ab$_1$ solution is 1-4 µg/mL, and the solvent is the 10 mmol/L PBS buffer solution with a pH value of 7.4.

5. The chemiluminescent immunoassay method according to claim 1, wherein in step ii), the oscillatory reaction is oscillatory reaction at 37° C. for 30 min on a magnetic rack, the cleaning is cleaning by the 10 mmol/L PBST solution with a pH value of 7.4 5 times, and the TSH-Ab$_1$-linked magnetic bead solution with a concentration of 1-2 mg/ml is obtained by re-dissolving in 100 µL of PBS solution.

6. The chemiluminescent immunoassay method according to claim 1, wherein in step iii), the solvent of the TSH antigen solution with the standard known concentration is the 10 mmol/L PBS buffer solution with a pH value of 7.4.

7. The chemiluminescent immunoassay method according to claim 1, wherein in step iii), specifically, 5-15 µL of TSH-Ab$_1$-linked magnetic bead solution and 15-25 µl of TSH antigen aqueous solution are evenly mixed with 130-150 µL of PBST buffer solution, 20-40 µL of CdTe NCs-labeled TSH-Ab$_2$ solution is added and evenly mixed, and oscillatory reaction is performed at room temperature for 4-5 min to obtain the immune complex solution.

* * * * *